United States Patent
Biggs

[11] Patent Number: 5,868,665
[45] Date of Patent: Feb. 9, 1999

[54] ENDOCOUPLER SYSTEM

[76] Inventor: Robert C. Biggs, 1005 Alderman Dr., Suite 101, Alpharetta, Ga. 30202

[21] Appl. No.: 777,549

[22] Filed: Dec. 30, 1996

[51] Int. Cl.$^6$ ....................................................... A61B 1/04
[52] U.S. Cl. ............................ 600/112; 600/160; 600/161
[58] Field of Search ....................................... 600/112, 109, 600/160, 161, 162, 173, 178, 182; 354/62

[56] References Cited

U.S. PATENT DOCUMENTS

| | | | |
|---|---|---|---|
| 5,101,807 | 4/1992 | Kawashima | 600/112 |
| 5,156,141 | 10/1992 | Krebs et al. | 600/112 |
| 5,349,942 | 9/1994 | Heinberger | 126/4 |
| 5,423,311 | 6/1995 | Smoke et al. | 128/6 |
| 5,429,604 | 7/1995 | Hammersmark | 604/95 |
| 5,435,805 | 7/1995 | Edwards et al. | 604/22 |

*Primary Examiner*—Beverly M. Flanagan

[57] ABSTRACT

An endocoupler system having an endocoupler (110) and a myeloscope (210). The present invention relates to an endocoupler system. More particularly, the present invention relates to an endocoupler system consisting of an endocoupler connected to a myeloscope. The present invention is a system to directly view the pathology of the epidural space in the lower spine region using a miniature endoscopic catheter device. This device is currently used by physicians to diagnose and treat patients who suffer from chronic low back pain. The present invention consists of a developed medical procedure, disposable procedure access kit, multi-lumen steerable catheter (Video Guided Catheter), small fiber optic endoscope (Myeloscope), endocoupler (Endocoupler), light source, and camera system. A major feature of the invention is the ability to orientate the viewing plane with respect to the image transmitted through the image fiber bundle by rotation of the image fiber coupler in a plane that is normal to the central optical axis of the objective lens assembly and image fiber coupler. This is accomplished in the present invention which is designed permitting the endocoupler to rotate allowing the image fiber coupling to be oriented at the connection point to the endocoupler. This is accomplished by means of a collet assembly which allows the user to loosen the collet and rotate the image fiber coupler to the desired orientation as viewed on the monitor and re-tighten the collet.

12 Claims, 4 Drawing Sheets

1

ENDOCOUPLER SYSTEM

BACKGROUND OF THE INVENTION

1. Field of the Invention

The present invention relates to an endocoupler system. More particularly, the present invention relates to an endocoupler system consisting of an endocoupler connected to a myeloscope.

2. Description of the Prior Art

The endocoupler system was developed to satisfy a need that every pain practitioner has faced for the last 60 years. The need to directly visualize the pathology in-situ in and around the nerve roots as they make their way out of neural forming along the axis of the spinal cord. Other means of visualizations such as Fluoroscopy, MRI and CAT Scans cannot produce real time images of the pathology or disease and cannot clearly differentiate soft tissue pathology. Epidural endoscopy was practically impossible if performed utilizing ridged optics and the paramedian or lumbar approach. This is due to the fact that the spinal cord is encased by an articulating bone structure with minimal access possibilities. Any device with the capability to access the epidural space would have to be flexible and very small. Using miniature fiberoptic endoscopes and miniature multi lumen steerable catheters the inventor has developed a medical device that introduces epidural space. The present invention allows physicians to directly visualize the epidural space of the spine and treat patients for related diseased in a minimally invasive manner.

Numerous innovations for an endoscope system have been provided in the prior art that are described as follows. Even though these innovations may be suitable for the specific individual purposes to which they address, they differ from the present invention as hereinafter contrasted.

In U.S. Pat. No. 5,435,805, titled Medical Probe Device with Optical Viewing Capability, invented by Stuart D. Edwards, Hugh R. Sharkey, Ingemar H. Lundquist, Ronald G. Lax and James A. Baker, Jr., a medical probe device comprising a catheter having a styler guide housing with at least one stylet port in a side thereof and stylet guide means for directing a flexible stylet outward through at least one stylet port and through intervening tissue to targeted tissues. The stylet guide housing has an optical viewing means positioned for viewing the stylet and adjacent structure which includes a fiber optic channel means for receiving a fiber optic viewing device. The fiber optic channel means can include a guide port means for directing longitudinal movement of a fiber optic device with respect to the stylet guide means in a viewing zone and a flushing liquid channel in the stylet guide housing having an exit port positioned to direct flushing liquid issuing therefrom across the end of a fiber optic device when positioned in the viewing zone. The optical viewing means can comprise a viewing window positioned in the stylet guide housing for viewing the stylet when it is directed outward from its respective stylet port. The optical viewing means can includes a fiber optic channel in the stylet guide housing for receiving the fiber optic, viewing device and aligning the viewing end thereof with the viewing window. Windowed devices can include a flushing liquid channel in the stylet guide housing having an exit port positioned to direct flushing liquid issuing therefrom across a surface of the viewing window.

In U.S. Pat. No. 5,429,604, titled Fiber Optic Catheter with Twistable Tip, invented by Dan J. Hammersmark, Timothy J. Wood, and Matthew S. Solar, the present invention is a catheter with a twistable tip. The catheter having a flexible wall for use in complex twisting anatomy contains a torque wire or a torquable guide wire lumen. The torque wire or torquable guide wire lumen extends through the length of the catheter and is attached to the catheter at or near the distal end thereof. The distal face of the catheter is angled to self align the catheter with an obstruction upon insertion. The proximal end of the torque wire protrudes from the proximal end of the catheter and is attached to a turn limiter. Rotation of the turn limiter imparts a torque to the torque wire or torquable guide wire lumen which is transmitted through the catheter to the distal end of the catheter where the applied torque twists the distal tip to manually align the tip with an obstruction. The twisting response at the tip of the catheter is determined by the torque applied to the torque element, the material and dimensional profile of the torque element, the attachment point of the torque element to the catheter and the material and dimensional profile of the catheter.

In U.S. Pat. No. 5,423,311, titled Catheter Imaging Apparatus, invented by Phillip J. Snoke, Stephen C. Gamper, David S. Rowley and Bruce W. Copeland, a catheter imaging apparatus for internally viewing body vessels or cavities, having a catheter, the catheter comprising a housing of such a size as to be readily held in the hand of a user, an elongate tube with one end connected to the housing and extending outwardly therefrom and being formed of material having sufficient stiffness to maintain the elongate tube in a substantially straight condition in the absence of an external force applied thereto, the elongate tube having a flexible distal end portion, guide wires having inner ends connected to the housing and extending outwardly therefrom through the elongate tube means, distal ends of the guide wires being connected to the flexible distal end portion of the elongate tube means, and a guide wire control carried by the housing and cooperating with proximal inner end portions of the guide wires for controlling the angular attitude of the flexible distal end portion of the elongate tube means, the guide wires and guide wire control cooperating to limit the angular attitude of the flexible distal end portion of the elongate tube to angular adjustments in a common plane extending generally parallel to the upper surface of the housing, and an imaging source for forming an image of an internal body cavity or vessel into which the catheter is inserted, the imaging means being in optical communication with the flexible distal end portion of the elongate tube of the catheter.

In U.S. Pat. No. 5,349,942, titled Flexible Endoscope, invented by Rudolf Helmberger, an endoscope with a flexible shaft, which consists of individual subassemblies releasably connected to each other. The proximal end of a flexible shaft is joined to a connecting portion and the distal end of the shaft can be steered into different positions by adjustment of an operating wire by means of an adjusting lever. The connecting portion can be coupled releasably to the distal end of the handle portion, at the proximal end of which an eyepiece portion is arranged. A hand-operated control means for the operating wire is provided in the handle portion, wherein the proximal end of the operating wire is clamped by a receiver in the control means. The receiver can be opened by operation of the adjusting lever for the purpose of releasing the above mentioned wire end, by moving the adjusting lever forwards of a neutral position. Moving the adjusting lever backwards from the neutral position effects longitudinal movement of the operating wire for controlling movement of the flexible shaft.

The above patented inventions differ from the present invention because the patented inventions each lack one or more of the following features which are described and claimed in the present invention: an endocoupler (110) which comprises: an endocoupler camera/eyepiece mount which is either an endocoupler camera mounting means or an endocoupler eyepiece viewing means consisting of an endocoupler eyepiece, an endocoupler eyepiece lens, and an endocoupler eyepiece lens holder, an endocoupler focus ring, an endocoupler body consisting of an endocoupler body objective lens assembly, an endocoupler body window holder, and an endocoupler body collet body, and an endocoupler collet knurled ring. A myeloscope is rotatably mounted to the endocoupler. The myeloscope consists of features such as: a myeloscope image coupler body having a myeloscope image coupler body male connector, a myeloscope fiberoptic endoscope consisting of a myeloscope fiberoptic endoscope distal end and a myeloscope fiberoptic endoscope light/image fiber bundle consisting of a myeloscope fiberoptic endoscope image fiber bundle and a myeloscope fiberoptic endoscope light fiber bundle, a myeloscope strain relief tubing, a myeloscope ACMI light port body having a myeloscope ACMI light port body attachment means, and a myeloscope fiber optic light guide scope lead having a myeloscope fiber optic light guide scope lead strain relief tubing.

Numerous innovations for an endoscope system have been provided in the prior art that are adapted to be used. Even though these innovations may be suitable for the specific individual purposes to which they address, they would not be suitable for the purposes of the present invention as heretofore described.

SUMMARY OF THE INVENTION

The present invention relates to an endocoupler system. More particularly, the present invention relates to an endocoupler system consisting of an endocoupler connected to a myeloscope. The present invention is a system to directly view the pathology of the epidural space in the lower spine region using a miniature endoscopic catheter device. This device is currently used by physicians to diagnose and treat patients who suffer from chronic low back pain. The present invention consists of a developed medical procedure, disposable procedure access kit, multi-lumen steerable catheter (Video Guided Catheter), small fiberoptic endoscope (Myeloscope), endocoupler (Endocoupler), light source, and camera system.

The myeloscope is a fiberoptic endoscope (scope) that is introduced through the one of the lumens in the video guided catheter. The fiberoptic endoscope relays the optical image to the endocoupler. The scope consists of an image fiber bundle and a light fiber bundle. The image fiber bundle is comprised of extremely small glass fibers (10,000 individual fibers in a ½ mm bundle) that are drawn in a coherent manner as to relay the image from the distal end of the scope to the image fiber coupler where the endoscope connects to the endocoupler. A small lens is mounted at the distal end of the scope to relay and focus the image to the fiberoptic image bundle. The light bundle is used to provide illumination at the distal end of scope for viewing. Both the image fiber bundle and the light fiber bundle are encased in flexible tubing and run parallel for the length of the scope. The two fiber bundles bifurcate at the image fiber coupler (body of the scope) where the image fiber terminates and the light fiber bundle passes to the light source.

The endocoupler is an optical device that is used to relay the image from the fiberoptic image bundle to the CCD camera. The endocoupler consists of a housing, objective lens set, and mechanical means to translate the objective lens set to focus the image. The objective lens set focuses on the image fiber bundle, magnifies the image, and projects the image to a CCD camera for viewing on a video monitor.

The video guided catheter is a four lumen catheter that incorporates the ability to steer the tip from left to right in one plane. The catheter consists of a body with integral steering mechanism and ports to access catheter lumens. The 0.100 inch diameter steerable catheter protrudes from the catheter body via a manifold that bifurcates the extruded catheter tubing into its four lumen components; two 0.014 inch diameter lumens for the steering wires, one 0.040 inch diameter lumen to pass the scope through the catheter, and one 0.040 inch diameter lumen for infusing fluids in the epidural space and passing instruments.

An access kit consists of disposable products that are used by the physician to access the epidural space through the sacral hiatus (tail bone). The kit contains drapes, syringe, needles, introducer set, etc.

The video system consists of a CCD camera, light source, and video monitor. The CCD camera is used to pickup the optical image from the endocoupler and convert it to an electronic signal that is sent to the video monitor. The light source consists of a bright light that is focused on the light fiber bundle to transmit light to the distal end of the scope.

The steerable catheter consists of a plastic body (handle), four lumen PeBax (plastic) extruded catheter shaft tubing, a system to bifurcate the four lumen catheter shaft to points of origin with in the housing, a mechanism to steer the catheter from left to right in one plane.

The endocoupler is used in conjunction with the video guided catheter is a Fiberscope that is inserted through one of the 0.040 diameter channels in the catheter and allows the physician to view images through the end of the catheter, hence "video guided catheter". The fiberoptic endoscope relays the optical image to the endocoupler. The fiberoptic endoscope consists of an image fiber bundle and a light fiber bundle. The image fiber bundle is comprised of extremely small glass fibers (10,000 individual fibers in a ½ mm bundle) that are drawn in a coherent manner as to relay the image from the distal end of the scope to the image fiber coupler where the endoscope connects to the endocoupler. A small lens is mounted at the distal end of the scope to relay and focus the image to the fiberoptic image bundle. The light bundle is used to provide illumination at the distal end of scope for viewing. Both the image fiber bundle and the light fiber bundle are encased in flexible tubing and run parallel for the length of the scope. The two fiber bundles bifurcate at the image fiber coupler (body of the scope) where the image fiber terminates and the light fiber bundle passes to the light source. The image fiber coupler in turn is connected to the endocoupler. A collet assembly is used to make the connection between the endocoupler and the image fiber coupler of the fiberoptic endoscope.

The endocoupler consists of a main body, focus ring, objective lens assembly, objective lens holder, window mount, collet body, collet nut, and either an eyepiece or C-mount. The endocoupler assembly provides for a mechanical means to translate the objective lens fore and aft within the endocoupler body to focus the image which is optically relayed to the video camera. The endocoupler connects to the video camera using an adapter which is threaded on to the rear of the endocoupler. The two adapters that adapt the endocoupler to the video camera are industry standard 32 mm eyepiece or C-mount adapter. The front of the endocoupler employs a collet assembly for connecting to the fiberoptic endoscope to the endocoupler. The collet assembly works in the same manner as a standard spring collet with clamping nut as readily used in machine tool holders. The configuration of the collet assembly is a tube that is angled at the top with walls that are slotted some distance down the length of the tube. Machined threads on the base of the tube are used for threading the clamping nut onto and over the tube. The inside diameter bore on the clamping nut employs an interfering angle to the angle on the collet tube. As the nut is advanced down the length of the tube, due to translation of the nut by mechanical means of a screw thread, the interfering angle in the bore of the clamping nut forces the walls on the tube to collapse which in turn decreases the inside diameter of the tube. The image fiber coupler on the fiberoptic endoscope has a boss which fits into the bore of the collet assembly on the endocoupler. The clamping nut is tightened to secure the scope to the endocoupler. By loosening the clamping nut with the boss of the image fiber coupler in the collet bore one can rotate the image fiber coupler about its central axis and re-tighten the clamping nut to orient the image fiber coupler at a different angle. This can be completed to orient the scope at any 360 degree angle with respect to the stationary endocoupler. By rotating the scope with respect to the stationary endocoupler allows the user to orient the viewing plane as seen on the video monitor in reference to actual spatial orientation of up and down. Once the proper orientation is set the image fiber bundle can be twisted in relation to the fixed end at the image fiber coupler/endocoupler connection and the actual orientation of the distal tip of the fiberoptic endoscope is displayed in proper orientation on the video monitor. This design feature is advantageous to the user since it allows him or her to maintain a proper reference of up and down when inside the epidural space of the spine where there is no readily evident spatial orientation signs. As the physician uses the scope in conjunction with the steerable catheter he or she may impose a set twist in the scope during a procedure due to the fact that the scope is restrained in rotation by wall friction of the channels and lumens in the steerable catheter. If a set twist develops in the image fiber bundle the physician can reorient the scope during the procedure by keying off certain pathology in which the orientation is known. Also, the steerable catheter may be withdrawn from the patient from time to time during the procedure to check spatial orientation and realign the scope if necessary.

The unique features are through the application of the present invention a need to be able to orient the viewing plane as seen on the monitor in relationship to the actual position of the distal end of the Fiberscope. To accomplish this, the present invention is designed permitting an user to rotate the image fiber coupler allowing the viewing plane to be oriented at the connection point to the endocoupler. This is accomplished by means of a collet assembly which allows the user to loosen the collet and rotate the image fiber coupler to the desired orientation as viewed on the monitor and re-tighten the collet. Currently, larger fiberoptic endoscopes place an orientation mark at the viewing end of the scope. However, due to the size of the fiber image bundle (0.5 mm) it is very difficult to place an orientation mark on either the fiber bundle or the lens.

The major patentable feature allows for orientation of the viewing plane with respect to the image transmitted through the image fiber bundle by rotation of the image fiber coupler in a plane that is normal to the central optical axis of the objective lens assembly and image fiber coupler.

METHOD OF UTILIZING THE ENDOCOUPLER SYSTEM

1. Connect the endocoupler to the camera system.
2. Open sterile camera drape package. Place sterile camera drape over the endocoupler assembly and place on the sterile field.
3. Open and place sterile fiberoptic endoscope on the sterile field. Inspect the surface of the endoscope visually for any tears or rough edges. Pay particular attention to the optic end of the scope since this is where most damage may occur.
4. Locate the fiberoptic light guide scope lead that has the stainless steel ACMI light port fitting connector. Pass this fitting to the circulating assistant to plug into the light source. If a light source adapter connector is used it should be screwed on to the ACMI light port fitting prior to plugging into the light source.
5. Locate the fiberoptic image coupler (black plastic connector with protruding boss). Grasp the endocoupler through the drape and loosen the knurled nut on the collet body. The front face of the knurled nut should be behind the front face of the collet for proper use. Insert the boss of the image fiber connector into the collet bor until the body of the connector seats on the front face of the collet. Tighten the knurled collet nut to retain image guide connector.
6. Turn Power On To All Components (camera system, light source, monitor, VCR or any other components that are connected in-line).
7. Adjust the light intensity on the light source if necessary. Light should now be emitting from the end of the flexible endoscope. If light is not emitting from the end of the flexible endoscope, make certain that light guide is seated properly in the selected light source outlet and the power is turned on.
8. Aim the flexible endoscope at a non-reflective object about one inch from the tip. Adjust the blue focusing ring on the endocoupler until you have a sharp, brilliant image on the monitor. The user should be able to focus on the end of the fiber bundle and see the faint outline of the individual fibers. If the user cannot obtain a sharp focused picture, check to see that the flexible endoscope connector is inserted into the collet bore until the body of the connector seats on the front face of the collet. If image is cloudy or hazy, clean both the distal end and image coupler end of the flexible endoscope with 70% isopropyl alcohol on a cotton swab and wipe dry.
9. The knurled collet nut on the endocoupler may be loosened and the fiberoptic image coupler rotated to align the viewing plane as seen on the monitor with respect to the orientation of the distal tip of the fiberoptic scope. Re-tighten the knurled collet nut to hold the fiberoptic image coupler in place. This process can be completed prior to the procedure to orient the image as seen on the monitor in relation to the video guided catheter, and during the procedure if necessary.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING

110—endocoupler (110)
112—endocoupler camera/eyepiece mount (112)
112A—endocoupler camera mounting means (112A)

112B—endocoupler eyepiece viewing means (112B)
112BA—endocoupler eyepiece (112BA)
112BB—endocoupler eyepiece lens (112BB)
112BC—endocoupler eyepiece lens holder (112BC)
114—endocoupler focus ring (114)
116—endocoupler body (116)
116A—endocoupler body objective lens assembly (116A)
116B—endocoupler body window holder (116B)
116C—endocoupler body collet body (116C)
118—endocoupler collet knurled ring (118)
210—myeloscope (210)
212—myeloscope image coupler body (212)
212A—myeloscope image coupler body male connector (212A)
214—myeloscope fiberoptic endoscope (214)
214A—myeloscope fiberoptic endoscope distal end (214A)
214B—myeloscope fiberoptic endoscope light/image fiber bundle (214B)
214BA—myeloscope fiberoptic endoscope image fiber bundle (214BA)
214BB—myeloscope fiberoptic endoscope light fiber bundle (214B1)
216—myeloscope strain relief tubing (216)
218—myeloscope ACMI light port body (218)
218A—myeloscope ACMI light port body attachment means (218A)
220—myeloscope fiber optic light guide scope lead (220)
220A—myeloscope fiber optic light guide scope lead strain relief tubing (220A)

BRIEF DESCRIPTION OF THE DRAWING

FIG. 3 is a longitudinal cross sectional view of an endocoupler along line 3—3 of FIG. 2.

DESCRIPTION OF THE PREFERRED EMBODIMENT

Figure 1:
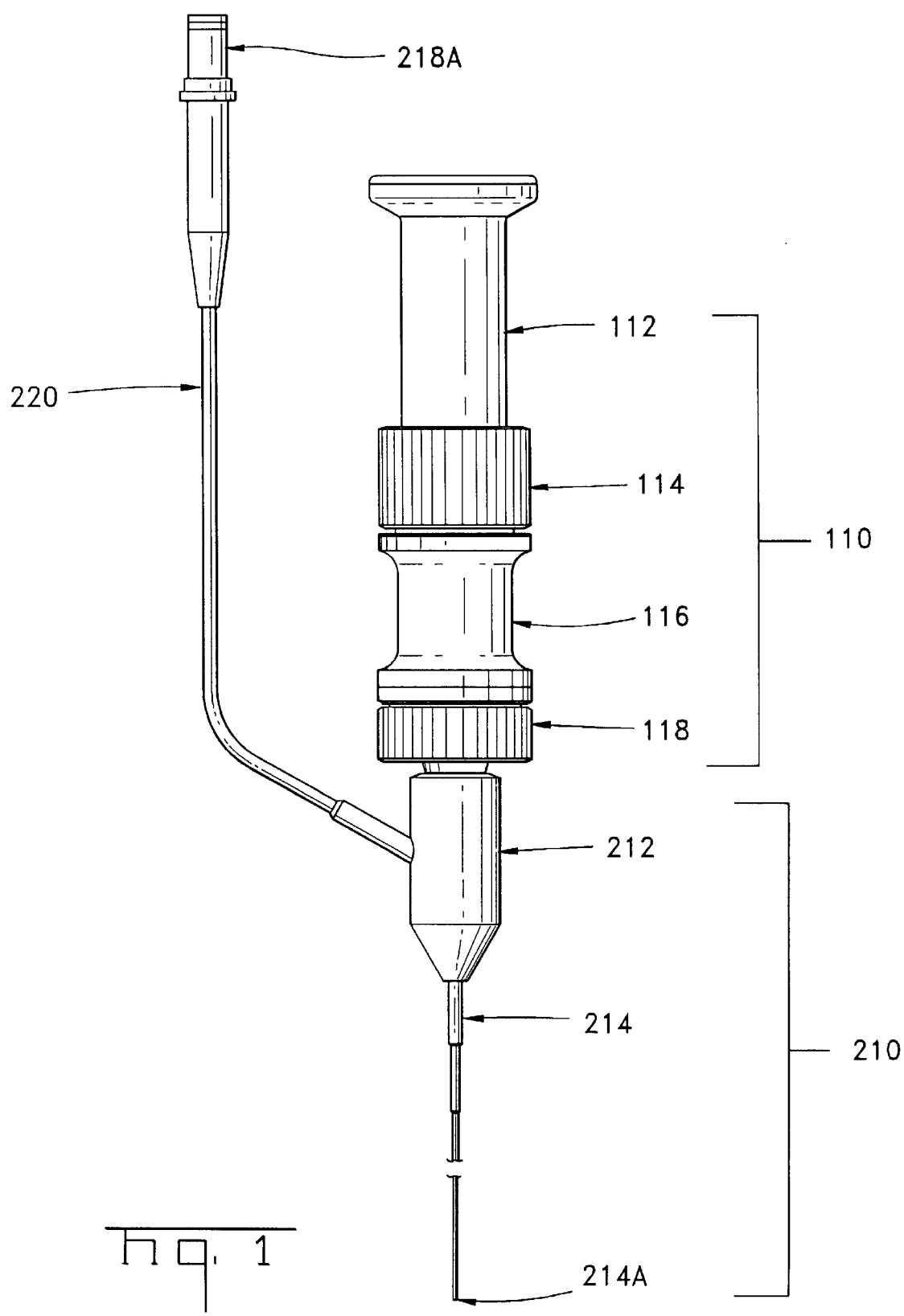
FIG. 1 is a top view of an endocoupler system exhibiting an endocoupler connected to a myeloscope.
Figure 2:
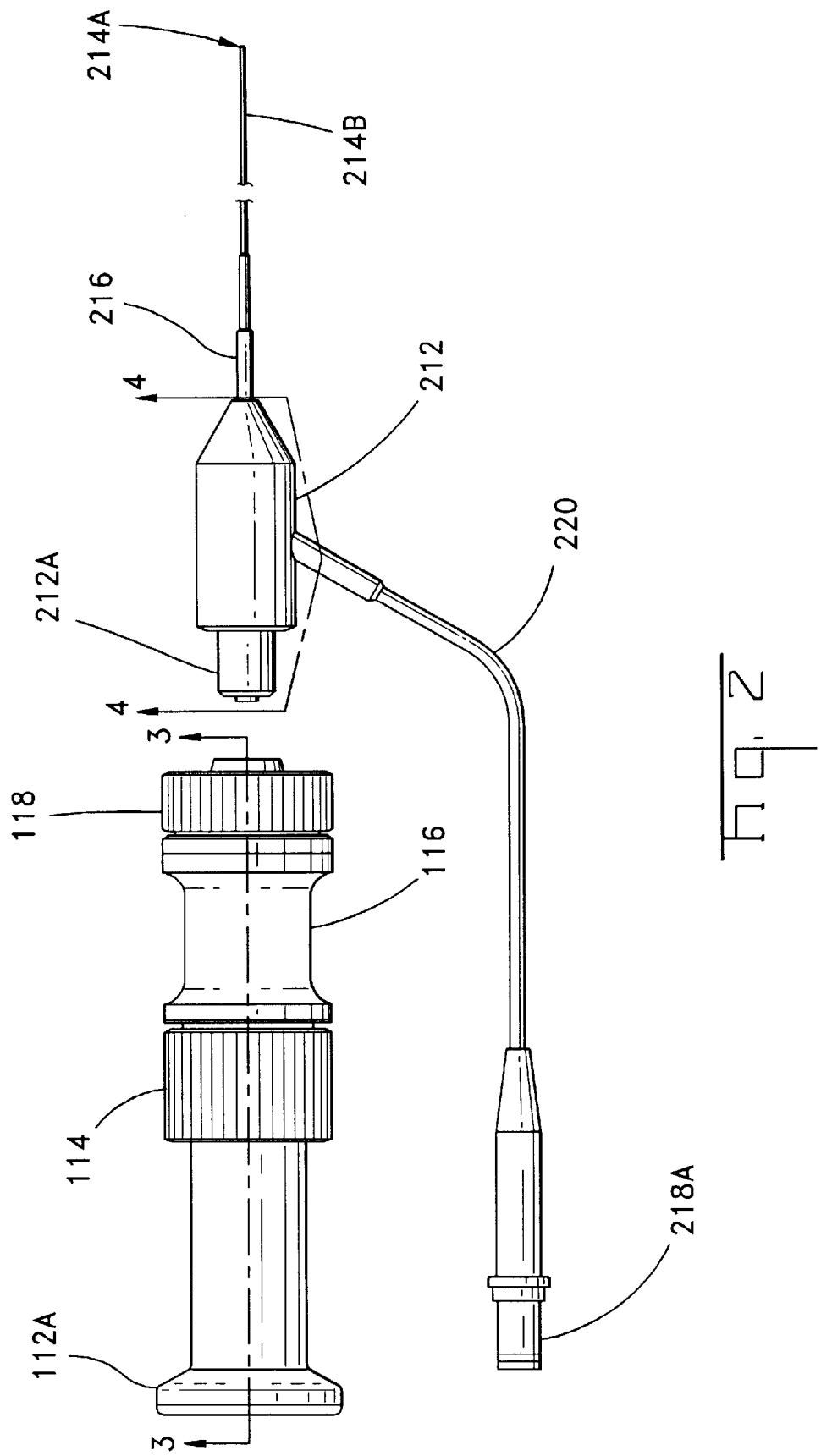
FIG. 2 is a side view of an endocoupler system exhibiting an endocoupler connected to a myeloscope.
Figure 7:
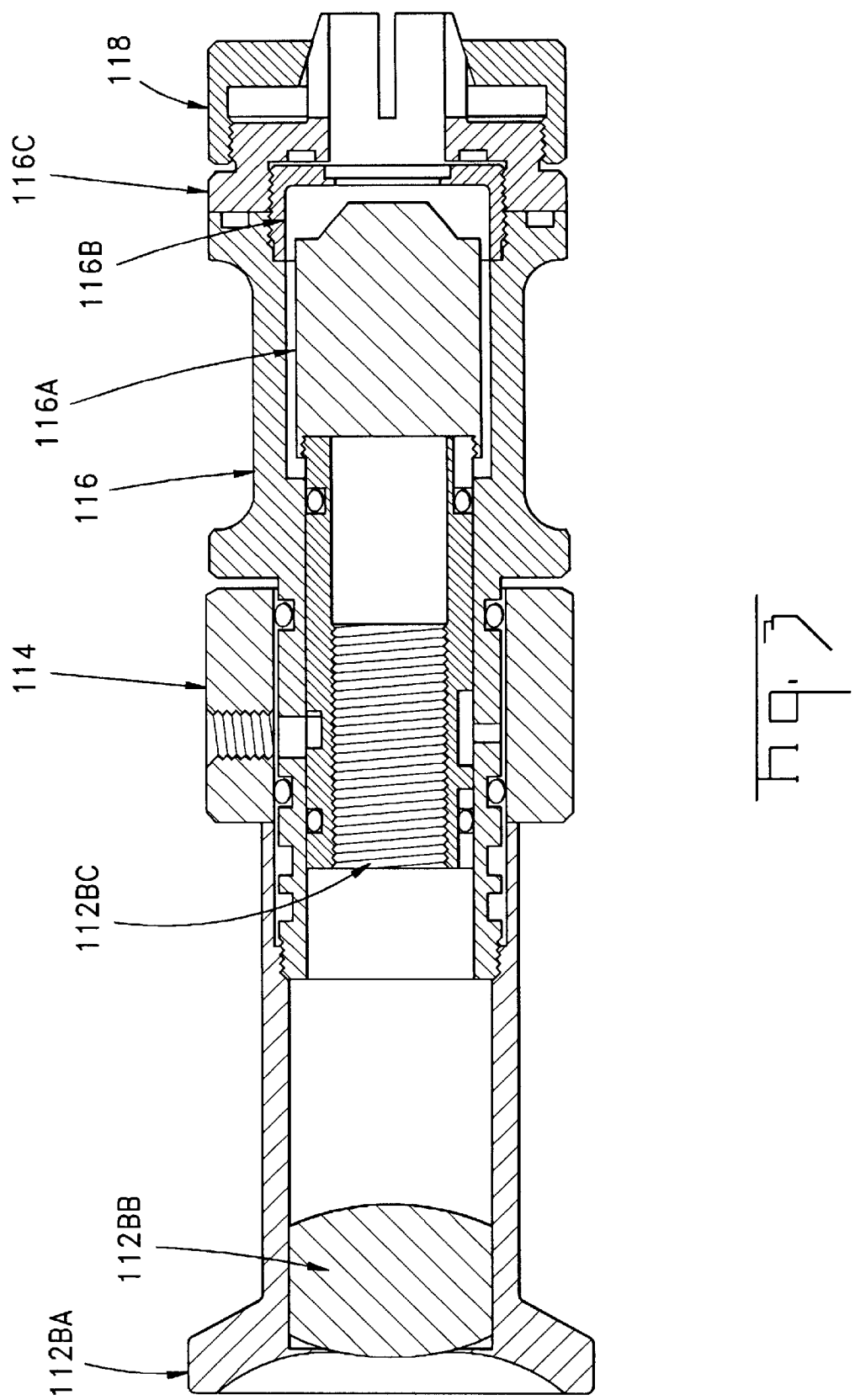

Firstly, referring to FIG. 1 and FIG. 2 which are a top view and side view, respectively, of an endocoupler system exhibiting an endocoupler (110) connected to a myeloscope (210). The myeloscope image coupler body (212) comprises a myeloscope image coupler body male connector (212A) positioned at a rear end thereof. The myeloscope image coupler body male connector (212A) is removably connectable to the endocoupler collet knurled ring (118).

Referring to FIG. 3 which is a longitudinal cross sectional view of an endocoupler (110) along line 3—3 of FIG. 2. The endocoupler system comprises an endocoupler (110) which comprises an endocoupler camera/eyepiece mount (112) securely mounted to an endocoupler focus ring (114) positioned at a front end thereto. The endocoupler focus ring (114) contains a threaded pin which engages the helical groove on the endocoupler eyepiece lens holder (112BC) to actuate the endocoupler eyepiece lens (112BB). The endocoupler camera/eyepiece mount (112) comprises a viewing means positioned at a rear distal end. The viewing means can optionally be an endocoupler camera mounting means (112A). The endocoupler camera mounting means (112A) is used to connect to video couplers on video camera systems. The viewing means can optionally be an endocoupler eyepiece viewing means (112B). The endocoupler eyepiece viewing means (112B) comprises an endocoupler eyepiece (112BA) securely fastened thereto and positioned at a rear distal end thereof. The endocoupler eyepiece viewing means (112B) further comprises a endocoupler eyepiece lens (112BB) securely mounted by an endocoupler eyepiece lens holder (112BC) contained within the endocoupler eyepiece viewing means (112B). The endocoupler eyepiece lens (112BB) is a lens selected from a group consisting of triplet and doublet. The endocoupler eyepiece lens (112BB) is preferably a HASTINGS (TM) Triplet Achromat Lens. The endocoupler eyepiece lens holder (112BC) has 180 degree helical groove machined at 6 degrees of lead to translate objective lens assembly to focus the image. The endocoupler eyepiece lens holder (112BC) has a 180 degree helical groove machined at 6 degrees of lead to translate endocoupler body objective lens assembly (116A) assembly to focus an image between the endocoupler eyepiece lens (112BB) and the endocoupler body objective lens assembly (116A).

The endocoupler (110) further comprises an endocoupler body (116) adjustably mounted to a front end of the endocoupler focus ring (114) endocoupler body (116) is a main housing of the endocoupler (110). The operator rotates the ring to focus the image as picked up by the CCD camera. The endocoupler body (116) comprises an endocoupler body objective lens assembly (116A) contained therein. An endocoupler body window holder (116B) is securely mounted at a front end of the endocoupler body objective lens assembly (116A) within the endocoupler body (116). The endocoupler body window holder (116B) is used to hold a clear round window to pass the image to the endocoupler eyepiece lens (112BB). The window is sealed to render the endocoupler (110) waterproof. An endocoupler body collet body (116C) is securely fastened to a front end of the endocoupler body (116). The endocoupler body collet body (116C) accepts myeloscope image coupler body male connector (212A). Clamps down on myeloscope image coupler body male connector (212A) to hold myeloscope (210) in place.

The endocoupler (110) further comprises an endocoupler collet knurled ring (118) is securely fastened to a front end of the endocoupler body collet body (116C). The endocoupler collet knurled ring (118) threads onto endocoupler body collet body (116C) and provides clamping force from tapered bore on nut compressing walls of endocoupler body collet body (116C).

Figure 4:
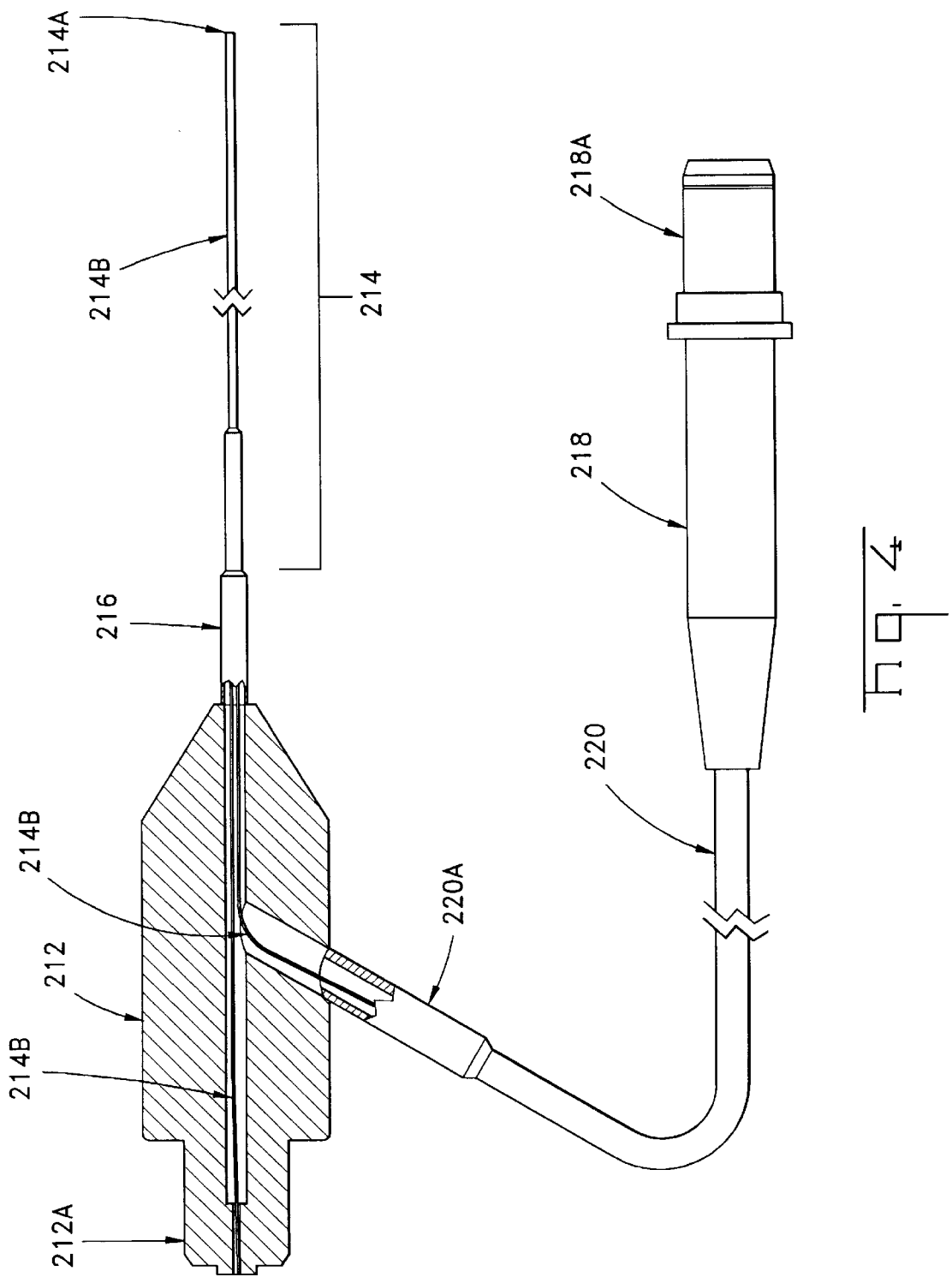
FIG. 4 is a partial longitudinal cross sectional view of a myeloscope along line 4—4 of FIG. 2.

Lastly, referring to FIG. 4 which is a partial longitudinal cross sectional view of a myeloscope (210) along line 4—4 of FIG. 2. The endocoupler system further comprises a myeloscope (210) which comprises a myeloscope image coupler body (212) having a longitudinal cavity there through connected to an angled cavity therein. The myeloscope image coupler body (212) comprises a myeloscope image coupler body male connector (212A) positioned at a rear end thereof. The myeloscope image coupler body male connector (212A) is removably connectable to the endocoupler body collet body (116). The myeloscope image coupler body (212) is the main body of myeloscope (210) where bifurcation of myeloscope fiberoptic endoscope image fiber bundle (214BA) and myeloscope fiberoptic endoscope light fiber bundle (214BB) occurs. The myeloscope fiberoptic endoscope light fiber bundle (214BB) transmits light to the myeloscope fiberoptic endoscope distal end (214A) from the illumination source. The myeloscope fiberoptic endoscope light/image fiber bundle (214B) is a sheathing that encapsulates both the myeloscope fiberoptic endoscope image fiber bundle (214BA) and myeloscope fiberoptic endoscope light fiber bundle (214BB) where they run parallel and terminate at the myeloscope fiberoptic endoscope distal end (214A).

The myeloscope (210) further comprises a myeloscope strain relief tubing (216) is securely fastened within a front distal end of the longitudinal cavity.

The myeloscope (210) further comprises a myeloscope fiberoptic endoscope (214) fastened to a front distal end of the myeloscope strain relief tubing (216). The myeloscope fiberoptic endoscope (214) comprises a myeloscope fiberoptic endoscope light/image fiber bundle (214B) fastened to a front distal end of the myeloscope strain relief tubing (216). The myeloscope fiberoptic endoscope (214) further comprises a myeloscope fiberoptic endoscope distal end (214A) securely fastened to a front distal end of the myeloscope strain relief tubing (216).

The myeloscope (210) further comprises a proximal distal end of a myeloscope fiber optic light guide scope lead strain relief tubing (220A) is securely fastened within the angled cavity.

The myeloscope (210) further comprises a proximal distal end of a myeloscope fiber optic light guide scope lead (220) is securely fastened to a distal end of the myeloscope fiber optic light guide scope lead strain relief tubing (220A).

The myeloscope (210) further comprises a proximal end of a myeloscope ACMI light port body (218) is securely fastened to a distal end of the myeloscope fiber optic light guide scope lead (220). The myeloscope ACMI light port body (218) comprises a myeloscope ACMI light port body attachment means (218A) positioned at a distal end thereof The myeloscope ACMI light port body (218) is where myeloscope fiberoptic endoscope light fiber bundle (214BB) in to myeloscope ACMI light port body attachment means (218A). The myeloscope ACMI light port body attachment means (218A) is an industry standard fitting that is used to plug into a wide variety of manufactures illumination sources.

The myeloscope (210) further comprises a myeloscope fiberoptic endoscope image fiber bundle (214BA) connected at a rear distal end to the myeloscope image coupler body male connector (212A) and further connected at a front distal end to the myeloscope fiberoptic endoscope distal end (214A). The myeloscope fiberoptic endoscope image fiber bundle (214BA) transcends through the myeloscope image coupler body (212) within the longitudinal cavity and myeloscope strain relief tubing (216) and the myeloscope fiberoptic endoscope (214). The myeloscope fiberoptic endoscope image fiber bundle (214BA) is a coherent bundle of small fiberoptic leads that optically transmits the image from myeloscope fiberoptic endoscope distal end (214A) to the bundle end in myeloscope image coupler body male connector (212A).

The myeloscope (210) further comprises a myeloscope fiberoptic endoscope light fiber bundle (214BB) connected at a rear distal end to the myeloscope ACMI light port body attachment means (218A) and further connected at a front distal end to the myeloscope fiberoptic endoscope distal end (214A). The myeloscope fiberoptic endoscope light fiber bundle (214BB) transcends through the myeloscope ACMI light port body (218) and the myeloscope fiber optic light guide scope lead (220) and the myeloscope fiber optic light guide scope lead strain relief tubing (220A) and the myeloscope image coupler body (212) angled cavity connected to the myeloscope image coupler body (212) longitudinal cavity and the myeloscope strain relief tubing (216) and the myeloscope fiberoptic endoscope (214).

It will be understood that each of the elements described above, or two or more together, may also find a useful application in other types of constructions differing from the type described above.

While the invention has been illustrated and described as embodied in an endoscope system, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

What is claimed is:

1. An endocoupler system comprising:
   A) an endocoupler which comprises;
      I) an endocoupler camera and eyepiece mount securely mounted to an endocoupler body positioned at a front end thereof, wherein the endocoupler camera and eyepiece mount comprises a viewing means positioned at a rear distal end thereof;
      ii) wherein the endocoupler body is mounted to an endocoupler focus ring and wherein an endocoupler objective lens holder moves inwardly and outwardly, the endocoupler body further comprises an endocoupler body objective lens assembly contained therein, and an endocoupler body window holder is securely mounted at a front end of the endocoupler body objective lens assembly within the endocoupler body;
      iii) an endocoupler body collet body securely fastened to a front end of the endocoupler body, and
      iv) an endocoupler collet knurled ring securely fastened to a front end of the endocoupler body collet body; and
   B) a myeloscope which comprises;
      I) a myeloscope image coupler body having a longitudinal cavity therethrough connected to an angled cavity therein, the myeloscope image coupler body further comprises a mycloscope image coupler body male connector positioned at a rear end thereof, the myeloscope image coupler body male connector is adjustably removably connectable to the endocoupler body collet body by the myeloscope image coupler body male connector;
      ii) a myeloscope strain relief tubing securely fastened within a front distal end of the longitudinal cavity;
      iii) a myeloscope fiberoptic endoscopic fastened to a front distal end of the myeloscope strain relief tubing, the myeloscope fiberoptic endoscope comprises a myeloscope fiberoptic endoscope light and image fiber bundle fastened to a front distal end of the myeloscope strain relief tubing, the myeloscope fiberoptic endoscope further comprises a myeloscope fiberoptic endoscope distal end securely fastened to a front distal end of the myeloscope strain relief tubing;
      iv) a proximal distal end of a myeloscope fiber optic light guide scope lead strain relief tubing securely fastened within the angled cavity;

v) a proximal distal end of a myeloscope fiber optic light guide scope lead is securely fastened to a distal end of the myeloscope fiber optic light guide scope lead strain relief tubing;

vi) a proximal end of a myeloscope ACMI light port body securely fastened to a distal end of the myeloscope fiber optic light guide scope lead, the myeloscope ACMI light port body comprises a myeloscope ACMI light port body attachment means positioned at a distal end thereof;

vii) a myeloscope fiberoptic endoscope image fiber bundle connected at a rear distal end to the myeloscope image coupler body male connector and further connected at a front distal end to the myeloscope fiberoptic endoscope distal end, the myeloscope fiberoptic endoscope image fiber bundle transcends through the myeloscope image coupler body within the longitudinal cavity and myeloscope strain relief tubing and the myeloscope fiberoptic endoscope, and viii) a myeloscope fiberoptic endoscope light fiber bundle connected at a rear distal end to the myeloscope ACMI light port body attachment means and further connected at a front distal end to the myeloscope fiberoptic endoscope distal end, the myeloscope fiberoptic endoscope light fiber bundle transcends through the myeloscope ACMI light port body and the myeloscope fiber optic light scope lead and the myeloscope fiber optic light guide scope lead strain relief tubing and the myeloscope image coupler body angled cavity connected to the myeloscope image coupler body longitudinal cavity and the myeloscope strain relief tubing and the myeloscope fiberoptic endoscope.

2. The endocoupler system as described in claim 1, wherein the viewing means is an endocoupler camera mounting means.

3. The endocoupler system as described in claim 1, wherein the viewing means is an endocoupler eyepiece viewing means.

4. The endocoupler system as described in claim 3, wherein the endocoupler camera and eyepiece mount comprises an endocoupler eyepiece securely fastened thereto and positioned at a rear distal end thereof, the endocoupler eyepiece viewing means further comprises an endocoupler eyepiece lens securely mounted with an endocoupler body.

5. The endocoupler system as described in claim 1, wherein the endocoupler eyepiece lens is a lens selected from a group consisting of triplet and doublet.

6. The endocoupler system as described in claim 1, wherein the endocoupler eyepiece lens holder has a 180 degrees helical groove machined at 6 degrees of lead to translate endocoupler body objective lens assembly to focus an image between the endocoupler eyepiece lens and the endocoupler body objective lens assembly.

7. The endocoupler system as described in claim 1, wherein the endocoupler focus ring contains a threaded pin which engages a helical groove on the endocoupler objective lens holder actuating the endocoupler body objective lens assembly.

8. The endocoupler system as described in claim 1, wherein the endocoupler body window holder holds a clear round window to pass the image to the endocoupler body objective lens assembly.

9. The endocoupler system as described in claim 8, wherein the window is sealed to render the endocoupler waterproof.

10. The endocoupler system as described in claim 1, wherein the endocoupler collet knurled ring threads onto the endocoupler body collet body providing clamping force from a tapered bore on a nut, which compresses walls of the endocoupler body collet body.

11. The he endocoupler system as described in claim 1, wherein the myeloscope image coupler body is the main body of myeloscope within which bifurcation of myeloscope fiberoptic endoscope image fiber bundle and myeloscope fiberoptic endoscope light fiber bundle occurs.

12. The endocoupler system as described in claim 1, wherein the myeloscope fiberoptic endoscope light and image bundle is a sheathing that encapsulates both the mycloscope fiberoptic endoscope image fiber bundle and the myeloscope fiberoptic endoscope light fiber bundle at a position where each runs parallel to the other terminating at the myeloscope fiberoptic endoscope distal end.

* * * * *